United States Patent [19]

Senda et al.

[11] Patent Number: 4,864,056

[45] Date of Patent: Sep. 5, 1989

[54] OPTICALLY ACTIVE HYDROXY ESTERS

[75] Inventors: Shuji Senda; Yutaka Nakazono, both of Osaka; Kenji Mori, Tokyo, all of Japan

[73] Assignee: Nitto Electric Industrial Co., Ltd., Osaka, Japan

[21] Appl. No.: 222,673

[22] Filed: Jul. 21, 1988

Related U.S. Application Data

[63] Continuation-in-part of Ser. No. 23,360, Mar. 9, 1987.

[30] Foreign Application Priority Data

Jul. 11, 1986 [JP] Japan ................... 61-164417

[51] Int. Cl.$^4$ .......................................... C07C 103/127
[52] U.S. Cl. ................................................... 560/179
[58] Field of Search ........................................ 560/179

[56] References Cited

PUBLICATIONS

Collin–Asselineau, Chemical Abstracts, vol. 55, No. 70946i (1961).

*Primary Examiner*—Bruce Gray
*Attorney, Agent, or Firm*—Sughrue, Mion, Zinn, Macpeak & Seas

[57] ABSTRACT

Methyl (2S,3S,4R)-(+)- and (2R,3R,4S)-(−)-3-hydroxy-2,4-dimethylheptanoates which are important intermediates for synthesis of invictolide, one component of a queen recognition pheromone of red imported fire ant.

5 Claims, 5 Drawing Sheets

OPTICALLY ACTIVE HYDROXY ESTERS

CROSS REFERENCE TO THE RELATED APPLICATION

This application is continuation-in-part application of U.S. patent application Ser. No. 023,360 filed Mar. 9, 1987, entitled "NOVEL OPTICALLY HYDROXY ESTER", which is now pending.

FIELD OF THE INVENTION

This invention relates to optically active hydroxy esters in substantially pure form. More specifically, it relates to methyl (2S, 3S, 4R)-(+)- and (2R, 3R, 4S)-(−)-3-hydroxy-2,4-dimethylheptanoates which are important intermediates for synthesis of invictolide, one component of a queen recognition pheromone of red imported fire ant (*Solenopsis invicta*).

BACKGROUND OF THE INVENTION

Red imported fire ant is insect pest which particularly causes enormous damage to agricultural crops in the U.S.A. As the use of agricultural chemicals has been restricted or even prohibited in recent years, it has been strongly desired to develop a new method of controlling this insect.

Controlling methods using various biologically active substances have been studied, and the use of pheromones has especially attracted attention. In particular, since the queen recognition pheromone is a pheromone by which worker ants recognize the queen, the use of such a queen recognition pheromone will permit an effective control of this insect species.

The queen recognition pheromone is composed mainly of the following three components:

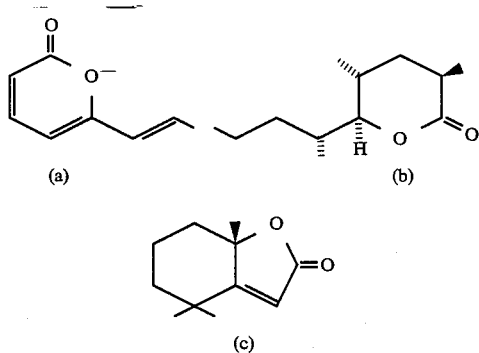

The compound (b) which is called invictolide is very difficult to synthesize stereoselectively since it contains four asymmetric carbons. The only prior report on its synthesis is Ziegler et al., *Tetrahedron Letters*, 27, 1229 (1986). However, this prior method of synthesis requires a number of steps and is difficult to employ industrially. Moreover, the invictolide obtained by this method has a low optical purity.

SUMMARY OF THE INVENTION

As a result of extensive investigations to establish a simple industrial process for producing optically active invictolide, the present inventors succeeded in obtaining a novel substance comprising optically active hydroxy esters in substantially pure form as a starting material for the stereoselective synthesis of invictolide. They have also found that by using these optically active hydroxy esters in substantially pure form, optically active invictolide having a high optical purity be easily produced by less process steps.

Accordingly, an object of this invention is to provide optically active hydroxy esters in substantially pure form, especially optically active methyl 3-hydroxy-2,4-dimethylheptanoate which is useful as a starting material easily producing optically active invictolide having a high optical activity. The optically active hydroxy esters in substantially pure form of this invention are represented by the following structural formula (I):

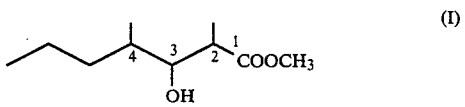

wherein the configuration of the 2,3 and 4 positions is (2S, 3S, 4R) or (2R, 3R, 4S).

Specifically, the present invention provides methyl (2S, 3S, 4R)-(+)-3-hydroxy-2-4-dimethylheptanoate of structural formula (Ia) and methyl (2R, 3R, 4S)-(−)-3-hydroxy-2-4-dimethylheptanoate of structural formula (Ib) as the optically active hydroxy ester in substantially pure form.

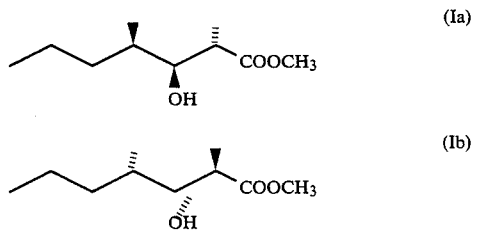

BRIEF DESCRIPTION OF THE ACCOMPANYING DRAWINGS

FIGS. 1, 2 and 3 are respectively the infrared absorption spectrum, proton nuclear magnetic resonance spectrum and $^{13}C$ nuclear magnetic resonance spectrum of substantially pure methyl (2S, 3S, 4R)-(+)-3-hydroxy-2-4dimethyheptanoate (Ia); and FIGS. 4 and 5 are respectively the infrared absorption spectrum and proton nuclear magnetic resonance spectrum of substantially pure methyl (2R, 3R, 4S)-(−)-3-hydroxy-2-4-dimethylheptanoate (Ib).

DETAILED DESCRIPTION OF THE INVENTION

Figure 1:
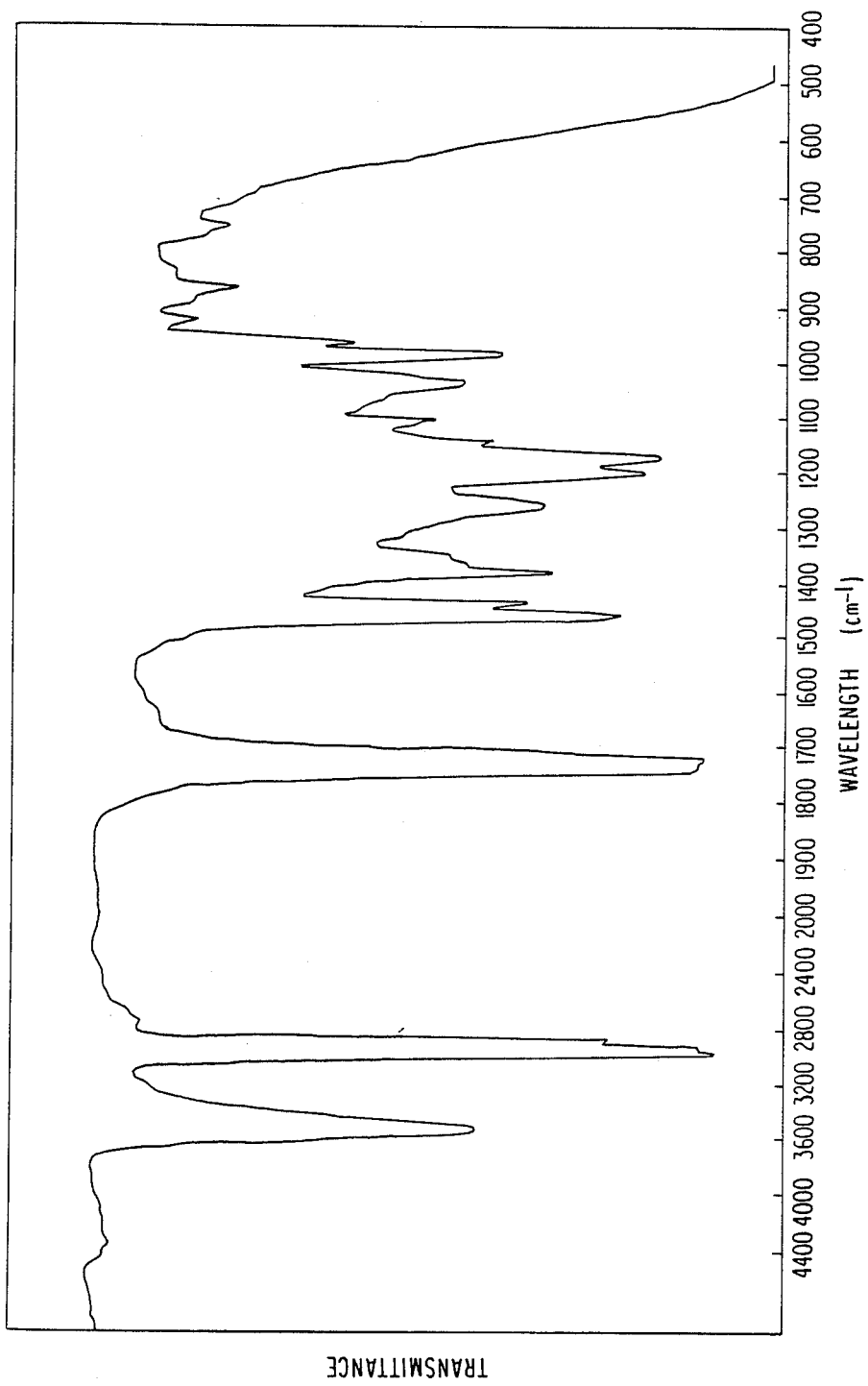

The optically active hydroxy ester in substantially pure form in accordance with this invention can be produced from the known optically active epoxide (2) in accordance with the following scheme (K. Mori et al., *Tetrahedron Letters*, 36, 2209 (1980)).

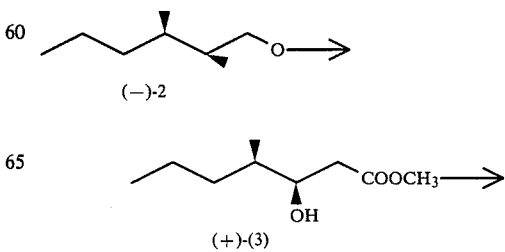

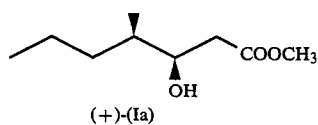

(+)-(Ia)

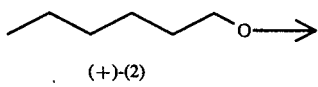

(+)-(2)

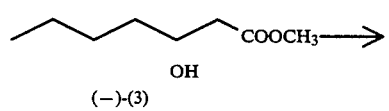

(−)-(3)

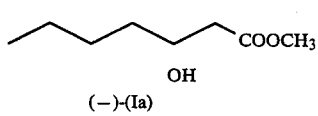

(−)-(Ia)

The epoxide (2) is first ring-opened with a cyanide ion and treated with acid to form a hydroxy acid. It is methyl-esterified to obtain the hydroxy ester (3). The hydroxy ester is then reacted with methyl iodide in the presence a base to α-methylate it and thus obtain the optically active hydroxy ester (Ia) in substantially pure form of the invention.

The production of the optically active hydroxy ester in substantially pure form of this invention will be described below in detail.

The optically active epoxide (2) can be obtained from the optically active amino acid (4), for example, in accordance with the method described in the above cited literature reference.

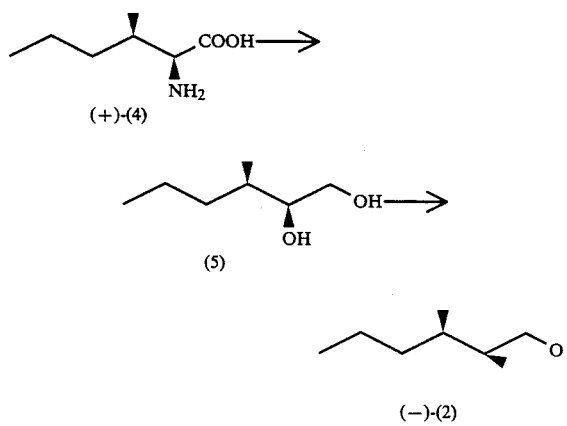

Likewise, (+)-(2) can be obtained from (−)-(4).

To ring-open the epoxide (2), the epoxide (2) is reacted with 1 to 10 equivalents, preferably 1.2 to 5 equivalents, based on the epoxide (2), of an alkali cyanide such as sodium cyanide or potassium cyanide in a solvent. There is no restriction on this solvent so long as it dissolves the epoxide (2) and the alkali cyanide used and does not inhibit the ring-opening reaction of the epoxide by the cyanide ion. Preferably, it is a lower aliphatic alcohol as methanol or ethanol, or its aqueous solution. The reaction temperature is from room temperature to the boiling point of the solvent used, preferably from 50° C. to the boiling point of the solvent. After the reaction, the reaction solution is concentrated and treated with an acid to obtain the hydroxycarboxylic acid. Methyl-esterification of the hydroxycarboxylic acid in a conventional manner gives the hydroxy ester (3).

The methyl group can be stereoselectively introduced into the carbon at the 2-position of the hydroxy ester (3) by the method of Frater (G. Frater, Helv., 62 6829 (1979)). For example, the hydroxy ester (3) is reacted with at least 2 equivalents, preferably 2 to 4 equivalents, of lithium diisopropylamide in a solvent, preferably at a low temperature of 0° C. or less, and then reacted with methyl iodide. In this reaction, the solvent is not particularly limited so long as it does not deleteriously affect the reaction. Usually, dry tetrahydrofuran is suitably used. The amount of methyl iodide used is at least 1 equivalent, preferably 1 to 3 equivalents, to the hydroxy ester. Preferably, the reaction is carried out at a temperature of 0° C. or less. The methylation reaction is stopped in a conventional manner, and then the optically active hydroxy ester (Ia) is isolated in substantially pure form by, for example, chromatography or distillation.

A process for producing methyl (2S,3S,4R)-3-hydroxy-2,4-dimethylheptanoate using (2S,3R)-1,2-epoxy-3-methylhexane as starting material according to the above-described manner is explained below.

(2S,3R)-1,2-Epoxy-3-methylhexane is reacted with an alkali cyanide to ring-open the (2S,3R)-1,2-epoxy-3-methylhexane, thereby obtaining the corresponding hydroxycarboxylic acid, the resulting hydroxycarboxylic acid is methyl-esterified in the conventional manner to obtain methyl (3R,4R)-3 hydroxy-4-methylheptanoate, the resulting ester is reacted with lithium diisopropylamide, and the resulting product is then reacted with methyl iodide to stereoselectively introduce a methyl group thereinto.

Further, a process for producing methyl (2R,3R,4S)-3-hydroxy-2,4-dimethylheptanoate using (2R,3S)-1,2-epoxy-3-methylhexane as a starting material according to the above-described manner is explained below.

(2S,3R)-1,2-Epoxy-3-methylhexane is reacted with an alkali cyanide to ring-open the (2R,3S) 1.2-epoxy-3-methylhexane, thereby obtaining the corresponding hydroxycarboxylic acid, the resulting hydroxycarboxylic acid is methyl-esterified in the conventional manner to obtain methyl (3S,4S)-3-hydroxy-4-methylheptanoate, the resulting ester is reacted with lithium diisopropylamide, and the resulting product is then reacted with methyl iodide to stereoselectively introduce a methyl group thereinto.

The optically active hydroxy ester in substantially pure form of the invention can be converted to invictolide in accordance with the following scheme.

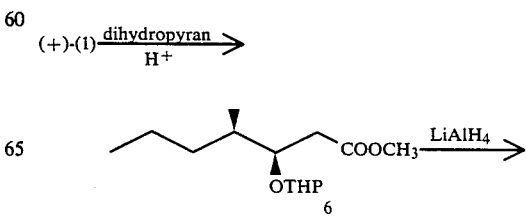

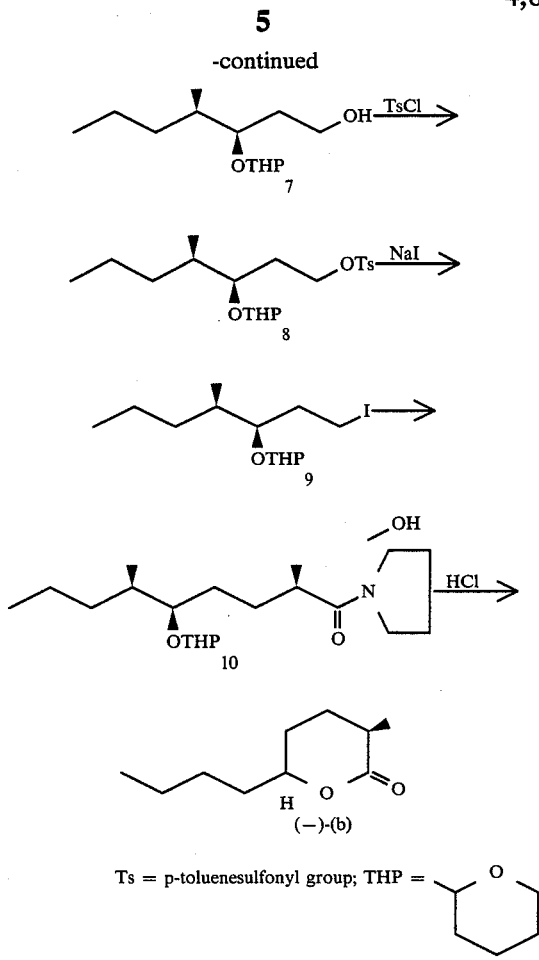

Ts = p-toluenesulfonyl group; THP = (tetrahydropyranyl)

Specifically, the optically active hydroxy ester (Ia) is reacted with dihydropyran in the presence of an acid catalyst to obtain the compound (6) having the protected hydroxyl group. The ester group of the compound (6) is then reduced with lithium aluminum hydride to obtain the compound (7). The compound (7) is tosylated and then iodinated. In accordance with the method of Evans et al. (*Tetrahedron Letters*, 24, 4233 (1980)), the product is subjected to asymmetric alkylation using propionamide of prolinol, and treated with an acid. As a result, elimination of the protective group, elimination of the prolinol and lactonization take place, and invictolide (b) in substantially pure form can be obtained.

By using the optically active hydroxy ester of the invention as a starting material, optically active invictolide having a high optical purity can be obtained by a smaller number of process steps.

The following examples illustrate the present invention more specifically.

Synthesis of methyl (+)-3-hydroxy-4-methylheptanoate(+)-(3)

720 mg (5.71 mmol) of (−)-epoxide (2) and 840 mg (17.1 mmol) of sodium cyanide were dissolved in 10 ml of a 40 % aqueous solution of ethanol, and the solution was refluxed for 6 hours. Then, ethanol was evaporated under reduced pressure. The aqueous layer was washed with ether and 2 N hydrochloric acid was added to the aqueous layer to adjust its pH to 3.5. The aqueous layer was then extracted with methylene chloride, dried over anhydrous sodium sulfate, filtered and concentrated to give 0.90 g of crude 3-hydroxy-4-methyheptanoic acid.

The crude product was treated with diazomethane, and distilled to give 560 mg (yield 56.3%) of methyl(+)3-hydroxy-2-4-dimethylheptanoate.

Synthesis of methyl (+)-3-hydroxy-2-4-dimethylheptanoate (−)-(3)

Methyl (31 )-3-hydoxy-2-4-dimethylheptanoate (−)(−3) was produced in a yield of 36% by operating in the same way as above except that (+)-epoxide (2) was used instead of (−) epoxide (2). Synthesis of Methyl (+)-3-hydroxy-2-4-dimethylheptanoate (Ia)

In 40 ml of dry tetrahydrofuran, 1.31 g (12.9 mmol) of diisopropylamine was reacted with 5.22 ml (1.65 N hexane solution, 8.61 mmol) of n-butyllithium at a temperature of −15° C. for 20 minutes to prepare a lithium diisopropylamide solution.

A solution of 500 mg (2.87 mmol) of methyl (+)-3-hydroxy-2-4-dimethylheptanoate(+)-(3) in 5 ml of dry tetrahydrofuran was added dropwise to the above lithium diisopropylamide solution at −65° C. over 1 minute in an atmosphere of nitrogen, and the mixture was maintained at 15° C. for 35 minutes. Then, 2.25 m (12.9 mmol) of hexamethylphosphoric triamide was added, and the temperature of the mixture was again adjusted to -65 ° C.

A solution of 1,027 mg (7.23 mmol) of methyl iodide in 5 ml of dry tetrahydrofuran was added dropwise at −65° C. for 2 minutes. The mixture was maintained at 131 65° C. for 4 hours , and then at −40° C. for 1 day, and further left to stand at −20 ° C. for 3 days. Thereafter, a saturated aqueous solution of ammonium chloride was added to stop the reaction. The reaction mixture was extracted with ether. The ethereal solution was washed with an aqueous solution of sodium chloride, dried over anhydrous magnesium sulfate, filtered, concentrated, and distilled to give 352 mg (yield 65.1%) of methyl (+)-3-hydroxy-2,4-dimethylheptanoate (Ia).

Figure 2:
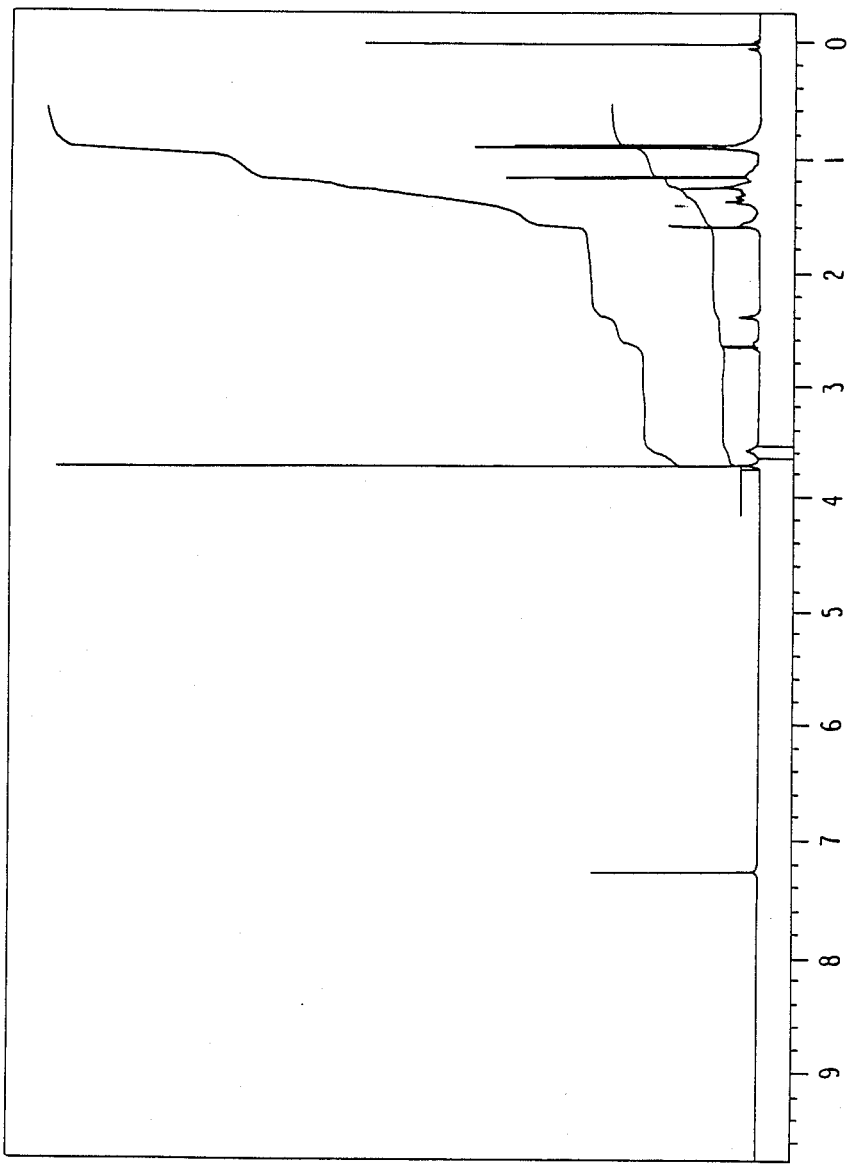
Figure 3:
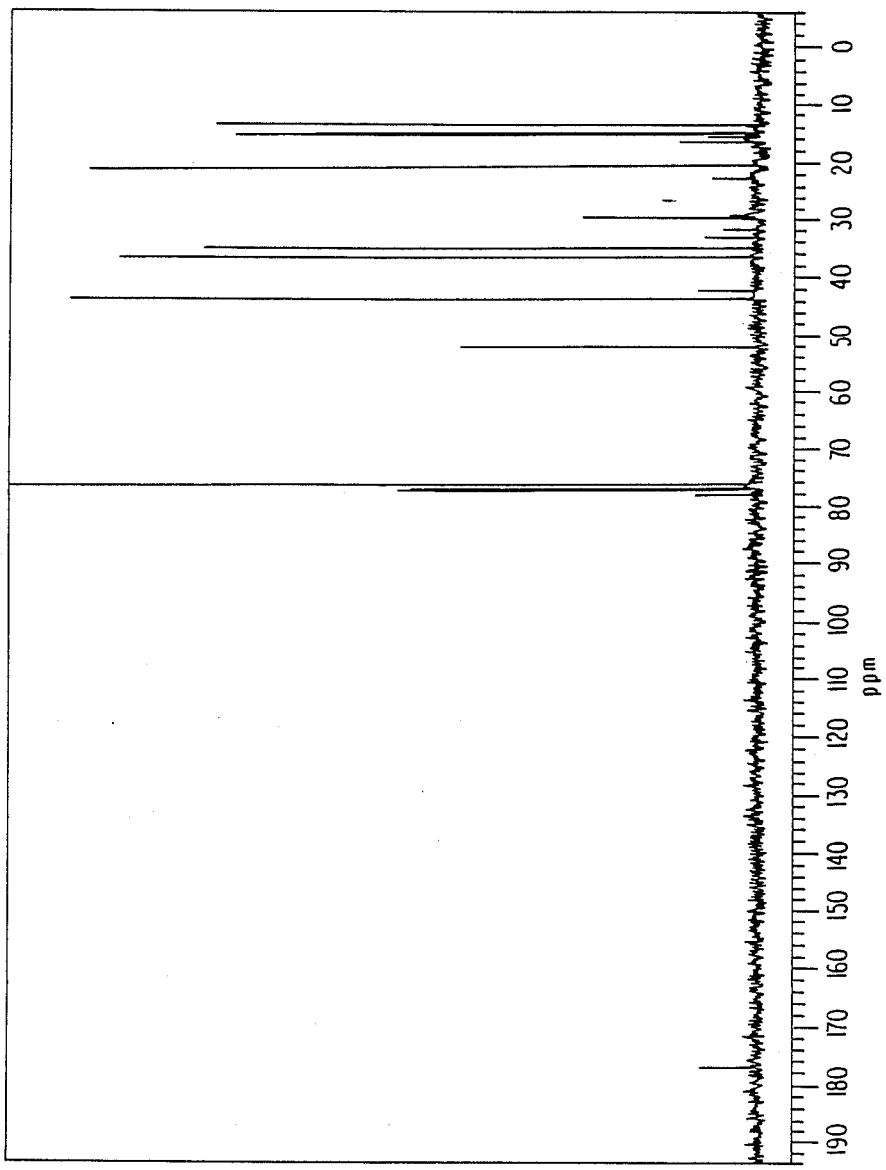

The infrared absorption spectrum, proton nuclear magnetic resonance spectrum and $^{13}C$. nuclear magnetic resonance spectrum (+)-3-hydroxy-2,4-dimethylheptanoate (Ia) are shown respectively in FIGS. 1, 2 and 3.

Boiling point: 75–78° C./1.5 mm Hg

| Elemental analysis ($C_{10}H_{20}O_3$): | | |
|---|---|---|
| | C | H |
| Found: | 63.52 | 10.88 |
| Calculated: | 63.79 | 10.71 |

IR absorption spectrum (neat): 3,520 (m), 2,960 (s), 2,930 (s), 2,880 (m), 1,725 (s), 1,460 (s), 1,435 (m), 1,380 (m), 1,260 (m), 1,200 (s), 1,170 (s), 1,140 (m), 1,105 (m), 1,030 (m), 980 (m), 955 (m), 915 (w), 55 (w), 740 (w)

$^1$H-NMR Spectrum (400 MHz, $CDCl_3$): 0.872 (3H, d, J=6.8 Hz), 0.904 (3H, t, J=7 Hz), 1.161 (3H, d, J=7.32 Hz), 1.18–1.43 (5H, m), 2.396 (1H, brd, J=6.4 Hz), 2.647 (1H, dq, J=7Hz, J =7Hz), 3.55–3.63 (1H, m), 3.714 (3H, s) $^{13}$C-NMR spectrum (100 MHz, $CDCl_3$): 12.774, 14.243, 14,468, 20.296, 34.762, 36.213, 43.091, 51.772, 76.067, 176.980

$[\alpha]_D^{26}+13.5°$ (c=0.555, $CHCl_3$)

Synthesis of methyl (−)-3-hydoroxy-2,4-dimethylheptanoate (Ib)

Methyl (−)-3-hydroxy-2,4-dimethylheptanoate (Ib) was produced in a yield of 57 % by operating in the same way as above except that methyl (−)-3-hydroxy-4-methylheptanoate (−)-(3) was used instead of methyl (+)-3-hydroxy-4-methylheptanoate.

Figure 4:
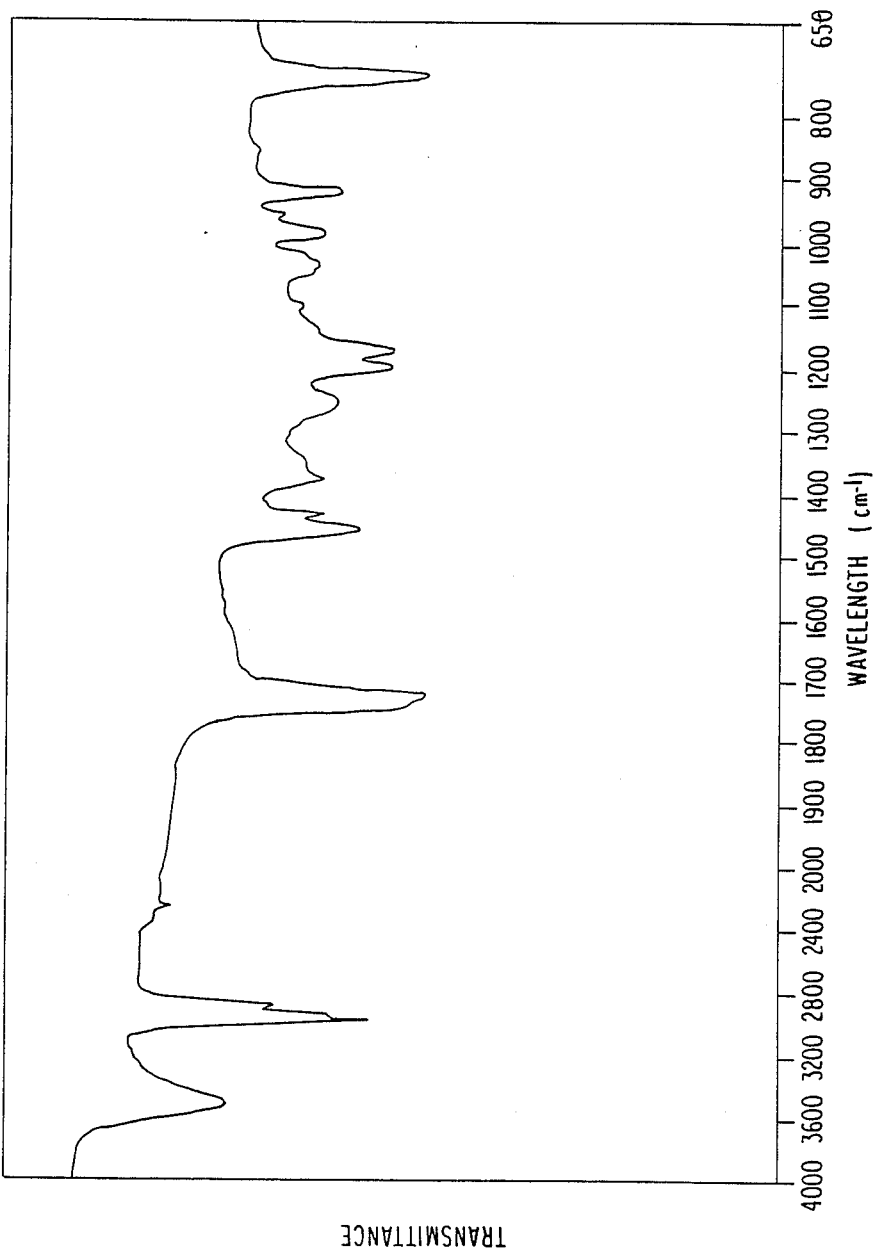
Figure 5:
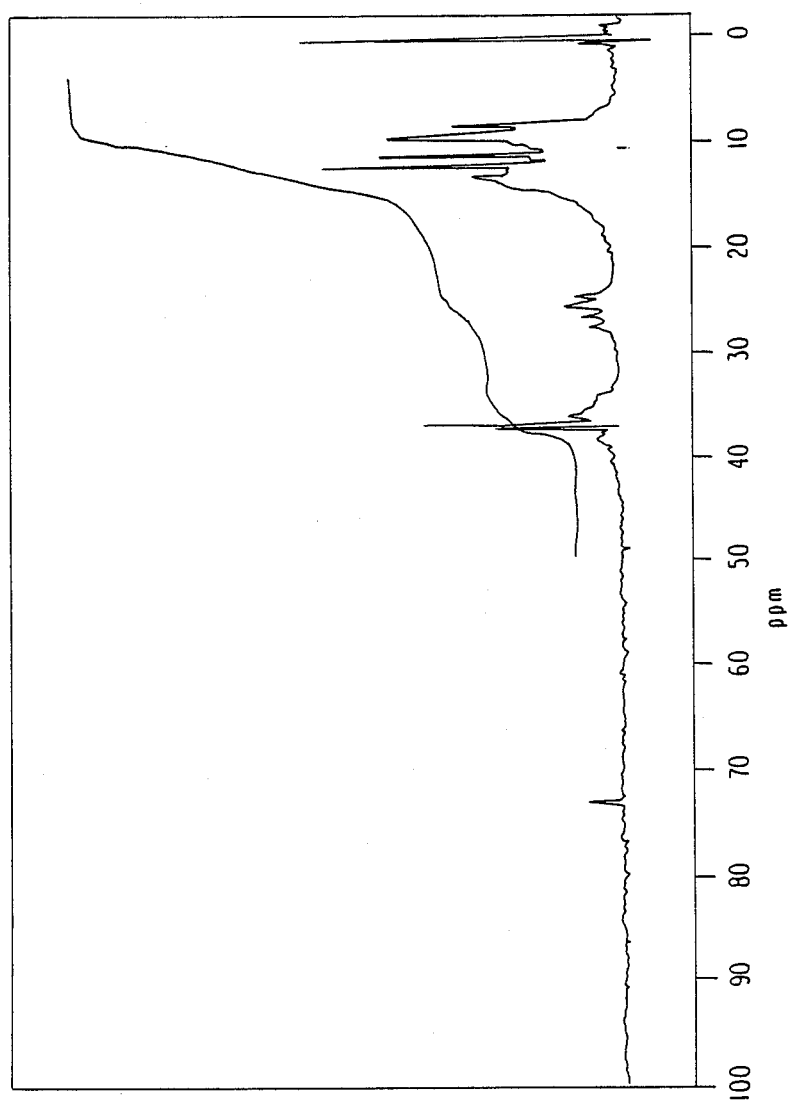

The infrared absorption spectrum and proton nuclear magnetic resonance spectrum of methyl (−)-3-hydroxy-2,4-dimethylheptanoate (Ib) are shown respectively in FIGS. 4 and 5.

Boiling point: 75° C./1.5 mm Hg $[\alpha]_D^{23}$: −15.1° (c=0.470, CHCl$_3$)

| Elemental analysis ($C_{10}H_{20}O_3$): | | |
|---|---|---|
| | C | H |
| Found: | 63.51 | 10.68 |
| Calculated: | 63.79 | 10.71 |

IR absorption spectrum (neat): Same as that of (+)-(Ia)

IH-NMR spectrum (400 MHz, CDCl$_3$): Same as that of (+)-(Ia)

An example of synthesis of (−)-invictolide (b) will be shown below.

Synthesis of (+)-2,4-dimethyl-3-tetrahydropyranyloxy-1heptanol (7)

200 mg (1.06 mmol) of methyl (+)-3-hydroxy-2,4-dimethylheptanoate was dissolved in 4 ml of tetrahydrofuran, and 134 mg (1.59 mmol) of dihydropyran and 1 mg of pyridinium p-toluenesulfonate were added, and the mixture was reacted overnight at room temperature. Since TLC showed that the starting materials still remained, 5 mg of pyridinium p-toluenesulfonate and 3 ml of methylene chloride were added, and the reaction was further carried out overnight at room temperature. The reaction mixture was extracted with ether. The ethereal layer was washed with a saturated aqueous solution of sodium hydrogencarbonate and then with an aqueous solution of sodium chloride, and dried over anhydrous sodium sulfate, filtered, and concentrated to give 350 mg of crude methyl (+)-2,4-dimethyl-3-tetrahydropyranyloxy-1heptanoate (6).

The crude reaction product (350 mg) was dissolved in 35 ml of ether, and under ice cooling, 80 mg (2.12 mmol) of lithium aluminum hydride was added. The mixture was maintained at room temperature for 3 hours, and 0.1 ml of water, a 10% aqueous solution of sodium hydroxide and then 0.3 ml of water were added to the reaction mixture. The precipitate was separated by filtration, concentrated and purified by chromatography (Wako Gel C-200 (10 g), hexane/ether) to give 260 mg (yield 96.9 %) of (+)-2,4-dimethyl-3-tetrahydropyranyloxy-1-heptanol (7).

Synthesis of 2,4-dimethyl-1-iodo-3-tetrahydropyranyloxyheptane (9)

230 mg (0.93 mmol) of the above compound (7) was dissolved in 2 ml of pyridine, and under ice cooling, 270 mg (1.41 mmol) of p-toluenesulfonyl chloride was added. Under ice cooling, the mixture was reacted for 3 hours, and then left to stand overnight at 3° C. The reaction mixture was put in water and extracted with ether. The ethereal layer was washed with 1 N hydrochloric acid, a saturated aqueous solution of copper sulfate, water, a saturated aqueous solution of sodium hydrogencarbonate and an aqueous solution of sodium chloride in this sequence, dried over anhydrous sodium sulfate, filtered and concentrated to obtain 330 mg of a crude tosylate (8).

The crude tosylate (8) (330 mg) was dissolved in 3 ml of dry dimethylformamide, and 170 mg (2 mmol) of sodium hydrogencarbonate and 212 mg (1.41 mmol) of sodium iodide were added to the solution. The mixture was reacted at room temperature for 3 days and further at 50 to 60° for 1 day. The reaction mixture was then put into water and extracted with benzene. The benzene layer was washed with an aqueous solution of sodium chloride, dried over anhydrous sodium sulfate, filtered, concentrated, and purified by chromatography (Wako Gel C-200 (10 g), to give 170 mg (yield from (7) 50.9%) of 2,4-dimethyl-1-iodo-3-tetrahydropyranyloxy-heptane (9).

Synthesis of 1-(5'-tetrahydropyranyloxy-2', 4', 6'-trimethylnonanoyl)-2-hydroxymethylpyrrolidine (10)

199 mg (1.97 mmol) of diisopropylamine was dissolved in 2.5 ml of dry tetrahydrofuran, and in an atmosphere of nitrogen, 0.795 ml of n-butyllithium (1.65 N hexane solution) was added dropwise at 1° C., and the mixture was maintained at 1° C. for 45 minutes. To the reaction mixture were added dropwise at 1° C. 68.7 mg (0.438 mmol) of (S)-(−)-prolinol propionamide and 0.5 ml of dry tetrahydrofuran, and the mixture was reacted at room temperature for 1 hour. To the reaction mixture was added dropwise 0.2 ml (1.15 mmol) of dry hexamethyl phosphoric amide, and the mixture was cooled to −100° C. Then, 112 mg (0.29 mmol) of the compound (9) was dissolved in 0.5 ml of dry tetrahydrofuran, and reacted at −100° C. for hours, and left to stand at −80° C. for 4 days. Water was added to the reaction mixture, and the mixture was extracted with ether. The ethereal layer was washed with 1 N hydrochloric acid and an aqueous solution of sodium chloride, dried over anhydrous magnesium sulfate, filtered, concentrated, and purified by chromatography (Wako Gel C-200 (3 g), hexane/ether/methanol) to give 97.0 mg (yield 86.6%) of compound (10).

Synthesis of (−)-invictolide (−)-(b)

90 mg (0.234 mmol) of the compound (10) and 1 N hydrochloric acid were mixed and refluxed for 2 hours. Chloroform was added, and the mixture was stirred at room temperature for 1 hour. The chloroform layer was separated, and the aqueous layer was further extracted with chloroform. All chloroform layers were collected, dried over anhydrous magnesium sulfate, filtered, concentrated, and purified by chromatography (Wako Gel C-200 (2 g), hexane/ether) to give 27.7 mg (yield 59.8%) of (−)-b.

| Elemental analysis ($C_{12}H_{22}O_2$): | | |
|---|---|---|
| | C | H |
| Found: | 72.47 | 11.35 |
| Calculated: | 72.68 | 11.18 |

IR absorption spectrum (neat): 2,960 (s), 2,930 (s), 2,870 (m), 1,740 (s), 1,460 (m), 1,380 (m), 1,330 (w), 1,235 (m), 1,195 (s), 1,150 (m), 1,120 (m), 1,090 (m), 1,020 (m), 990 (m), 720 (w)

IH-NMR spectrum (400 MHz, CDCl$_3$) 0.903 (3H, t, J=7.5 Hz), 0.914 (3H, D, J=6.8 Hz), 1.219 (3H, d, J=6.8 Hz), 1.25–1.51 (4H, m), 1.65–1.74 (3H, m), 1.86–2.05 (1H, m), 28.5–2.70(1H, m), 3.900 (1H, d, d→q, J=2Hz, J=10Hz)

IH-NMR spectrum (400 MHz, C$_6$D$_6$) 0.456 (3H, d, J=6.8 Hz), 0.814 (3H, d, J=6.5 Hz), 0.870 (3H, t, J=7.2 Hz), 0.989 (1H, ddd, J=7Hz, 8Hz, 13.5Hz), 1.068 (3H, d, J=7Hz), 1.096–1.300(3H, m), 1,318–1.443 (3H, m), 1.508 (1H, dddq, J=7.5Hz, J=7.5Hz, J=10Hz, J=7Hz), 2.040 (1H, ddg, J=8 Hz, J=9Hz, J=7Hz), 3.442 (1H, dd, J=0.8Hz, J=10Hz) $^{13}$C-NMR spectrum (100 MHz, CDCl$_3$): 12.349, 14.164, 16.622, 17.697, 20.465, 28.436, 32,558, 33,693, 35.484, 36.140, 85.737, 176.682

Gas chromatography (Carbowax 20 M, 0.2 mm×25 m, 120° C.→140° C., 3° C./min, He 0.7 ml/min):

Rt 9.66 min (98.2%) $[\alpha]_D^{27}$: −105° (c=0.29, CHCl$_3$)

Synthesis of (+)-invictolide (b)

(−)-invictolide (b) was produced by operating in the same way as above except that (−)-(Ib) was used instead of (+)-(Ib).

$[\alpha]_D^{22}$: +101° (c=0.615, CHCl$_3$)

| Elemental analysis (C$_{12}$H$_{22}$O$_2$) | | |
|---|---|---|
| | C | H |
| Found: | 72.51 | 11.15 |
| Calculated: | 72.68 | 11.18 |

Determination of Optical Purity of Hydroxy Esters

The Determination of the optical purity of compositions containing hydroxy esters represented by the formulae (Ia) and (Ib)

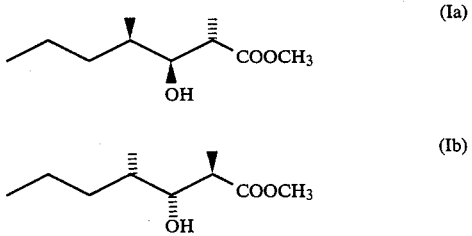

is according to MTPA (α-methoxy-α-trifluoromethyl phenylacetic acid) ester method by J. A. Dale et al, text of which is incorporated herein by reference.

The measurement method is explained by reference to Compound (Ia) above.

Compound (Ia) is converted to its MTPA ester (A) using an acid chloride derived from (+)-(α)-methoxy-α-trifluoromethylphenylacetic acid. At the same time, any Compound (Ib) contained with the Compound (Ia) component is converted to its MTPA ester (B).

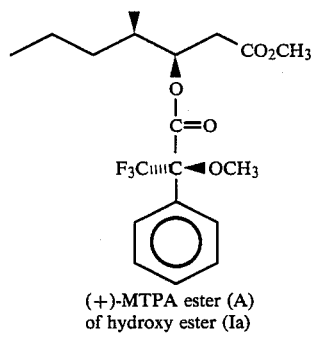

(+)-MTPA ester (A)
of hydroxy ester (Ia)

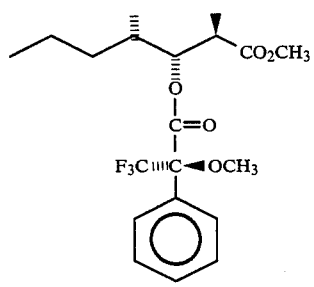

(+)-MTPA ester (B)
of hydroxy ester (Ib)

The resulting esters (A) and (B) have the relationship of diastereomers.

The esters (A) and (B) thus obtained are separated by, for example, liquid chromatography. The optical purity of ester is calculated by comparison of the area of the liquid chromatography peak of the separated ester to the liquid chromatography peak of the original mixture.

Determination of Optical Purity of Hydroxy Esters (Ia) and (Ib)

5 mg of the hydroxy ester (Ia) was dissolved in 0.1 ml of pyridine, and 10 μl of (+)-α-methoxy-α-trifluoromethylphenylacetic acid chloride was added thereto to conduct reaction overnight at room temperature. The resulting reaction mixture was poured into water and extracted with ether. The extract was washed with diluted hydrochloric acid and a saturated NaCl aqueous solution, and then dried with sodium sulfate anhydride. The material thus obtained was filtered and concentrated to obtain a sample for analysis.

The same procedure as above was followed except for using the hydroxy ester (Ib) in place of the hydroxy ester (Ia) to obtain a sample for analysis.

Using those two samples obtained above, the optical purity of each of the hydroxy esters (Ia) and (Ib) was determined according to the determination described above using a liquid chromatograph under the following conditions.

Column: NUCLEOSIL 50-7, 25 cm (height)×4.6 mm (diameter)
Solvent: Hexane/THF =99/1
Flow Rate: 1 ml/min
Detector: UV 254 nm The results obtained are shown below.

Hydroxy Ester (Ia)
RT: 29.9 min (1%)

98% ee(Residual 2%: racemic

| | -continued | |
|---|---|---|
| 32.7 min (99%) | form) | |
| Hydroxy Ester (Ib) | | |
| RT: 29.3 min (98.5%) | | |
| 32.1 min (1.5%) | 97% ee(Residual 3%: racemic form) | |

While the invention has been described in detail and with reference to specific embodiments thereof, it will be apparent to one skilled in the art that various changes and modifications can be made therein, without departing from the spirit and scope thereof.

What is claimed is:

1. A substance selected from the group consisting of (2S,3S,4R) or (2S,3R,4S) hydroxy ester represented by the structural formula

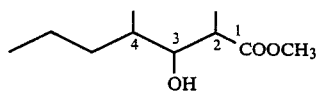
(I)

said substance being in substantially pure form and being substantially free from its optical enantiomer.

2. A (2S,3S,4R) hydroxy ester represented by the structural formula

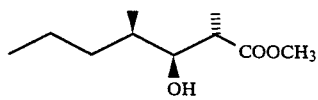
(Ia)

said hydroxy ester being in substantially pure form and being substantially free from its optical enantiomer.

3. A (2R,3R,4S) hydroxy ester represented by the structural formula

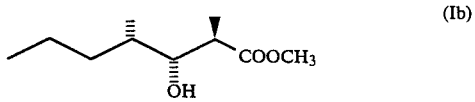
(Ib)

said hydroxy ester being in substantially pure form and being substantially free from its optical enantiomer.

4. A process for producing methyl (2S,3S,4R)-3-hydroxy-2,4-dimethylheptanoate, which comprises reacting (2S,3R)-1,2-epoxy-3-methylhexane with an alkali cyanide to ring-open the (2S,3R)-1,2-epoxy-3-methylhexane, thereby obtaining the corresponding hydroxycarboxylic acid, esterifying the resulting hydroxycarboxylic acid to obtain methyl (3R,4R)-3-hydroxy-4-methylheptanoate, reacting the resulting product with lithium diisopropylamide, and then reacting the resulting product with methyl iodide to stereoselectively introduce a methyl group thereinto.

5. A process for producing methyl (2R,3R,4S)-3-hydroxy-2,4-dimethylheptanoate, which comprises reacting (2R,3S)-1,2-epoxy-3-methylhexane with an alkali cyanide to ring-open the (2R,3S)-1,2-epoxy-3-methyhexane, thereby obtaining the corresponding hydroxycarboxylic acid, esterifying the resulting hydroxycarboxylic acid to obtain methyl (3S,4S)-3-hydroxy-4-methylheptanoate, reacting the resulting product with lithium diisopropylamide, and then reacting the resulting product with methyl iodide to stereoselectively introduce a methyl group thereinto.

* * * * *